(12) United States Patent
Suh et al.

(10) Patent No.: US 7,067,553 B2
(45) Date of Patent: *Jun. 27, 2006

(54) THIOUREA COMPOUNDS AND THE PHARMACEUTICAL COMPOSITIONS CONTAINING THE SAME

(75) Inventors: Young Ger Suh, Kyunggi-do (KR); Uh Taek Oh, Kyunggi-do (KR); Hee Doo Kim, Seoul (KR); Jee Woo Lee, Seoul (KR); Hyeung Geun Park, Seoul (KR); Young Ho Park, Seoul (KR); Jung Bum Yi, Kyunggi-do (KR)

(73) Assignee: Pacific Corporation, Kyunggi-do (KR)

( * ) Notice: Subject to any disclaimer, the term of this patent is extended or adjusted under 35 U.S.C. 154(b) by 14 days.

This patent is subject to a terminal disclaimer.

(21) Appl. No.: 10/362,079

(22) PCT Filed: Aug. 20, 2001

(86) PCT No.: PCT/KR01/01408

§ 371 (c)(1),
(2), (4) Date: Feb. 20, 2003

(87) PCT Pub. No.: WO02/16319

PCT Pub. Date: Feb. 28, 2002

(65) Prior Publication Data

US 2003/0212140 A1    Nov. 13, 2003

(30) Foreign Application Priority Data

Aug. 21, 2000 (KR) .............................. 2000-48385

(51) Int. Cl.
A61K 31/165 (2006.01)
A61K 31/195 (2006.01)
C07C 21/22 (2006.01)

(52) U.S. Cl. .................. 514/476; 564/27; 564/372; 564/32; 564/39; 564/47

(58) Field of Classification Search .............. 564/32, 564/39, 47
See application file for complete search history.

(56) References Cited

U.S. PATENT DOCUMENTS

| 3,117,994 | A | 1/1964 | McKay et al. | |
|---|---|---|---|---|
| 3,546,344 | A | 12/1970 | Martin et al. | |
| 4,460,602 | A | 7/1984 | Buckwalter et al. | |
| 5,403,868 | A | 4/1995 | Reid et al. | |
| 5,780,483 | A | 7/1998 | Widdowson et al. | |
| 6,057,451 | A | 5/2000 | Crute et al. | 548/194 |
| 6,288,091 | B1 | 9/2001 | Crute et al. | 514/346 |
| 2003/0153596 | A1 | 8/2003 | Suh et al. | |
| 2003/0203944 | A1 | 10/2003 | Suh et al. | |

FOREIGN PATENT DOCUMENTS

| EP | 0 405 233 B1 | 10/1993 |
|---|---|---|
| EP | 0 462 933 B1 | 6/1994 |
| EP | 0 528 146 B1 | 2/1996 |
| GB | 2 168 975 A | 7/1986 |
| GB | 2 206 347 A | 1/1989 |
| JP | 11-35545 | 2/1999 |
| WO | WO 99/00115 * | 1/1999 |
| WO | WO 99/37675 | 7/1999 |
| WO | WO 00/50387 | 8/2000 |
| WO | WO 02/08221 A2 | 1/2002 |
| WO | WO 02/072536 A1 | 9/2002 |
| WO | WO 02/076946 A2 | 10/2002 |
| WO | WO 02/090326 A1 | 11/2002 |
| WO | WO 03/014064 A1 | 2/2003 |

OTHER PUBLICATIONS

Lee et al., 1995, Bioorg. Med. Chem. Lett. 5, pp. 1331-1334.
Szallasi and Blumberg, 1999, Pharm. Rev. 51, pp. 159-211.
Wrigglesworth and Walpole, 1998, Drugs of the Future 23, pp. 531-538.
Wood et al., 1998, J. Neurosci. 8 pp. 3208-3220.
Caterina et al., 1997, Nature 389, pp. 816-824.
Tominaga et al., 1998, Neuron 21, pp. 531-543.
Caterina et al., 2000, Science 288, pp. 306-313.
Davis et al., 2000, Nature 405, pp. 183-187.
Hwang et al., 2000, PNAS 97, pp. 6155-6160.
Zygmunt et al, 2000, Trends Pharmacol. Sci, 21, pp. 43-44.
Ren et al., 2000, Dig. Dis. Sci. 45, pp. 830-836.
Perkins and Campbell, 1992, Br. J. Pharmacol. 107, pp. 329-333.
Kwak et al., 1998, Neurosci. 86, pp. 619-626.
Santos and Calixto, 1997, Neurosci. Lett. 235, pp. 73-76.
McDonnell et al., 2002, Bioorg. Med. Chem. Lett. 12, pp. 1189-1192.
Lee et al., 2002, Bioorg. Med. Chem. Lett. 10, pp. 1171-1179.
Lee et al., 2001, Bioorg. Med. Chem. Lett. 9, pp. 1713-1720.
Wahl et al., 2001, Mol. Pharmacol. 59, pp. 9-15.
Domenico Spina et al., Pharmacology of airway irritability, pp. 264-272.

(Continued)

Primary Examiner—Cecilia Tsang
Assistant Examiner—Lexington Hoffman
(74) Attorney, Agent, or Firm—Finnegan, Henderson, Farabow, Garrett & Dunner, L.L.P.

(57) ABSTRACT

The present invention relates to thiourea compounds and the pharmaceutical compositions containing the same, and particularly, to novel thiourea compounds as an antagonist against vanilloid receptor (VR) and the pharmaceutical compositions thereof. As diseases associated with the activity of vanilloid receptor, pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and inflammatory diseases can be enumerated. The present invention provides a pharmaceutical composition for prevention or treatment of these diseases.

6 Claims, No Drawings

OTHER PUBLICATIONS

Jeewoo Lee et al., *Bioorganic & Medicinal Chemistry*, 9 (2001) 19-32.

Yun Wang et al., *Molecular Pharmacology*, vol. 62. No. 4, pp. 947-956 (2002).

Jung Wha Yoon et al., *Bioorganic & Medicinal Chemistry Letters*, 4 pp. (Article in Press).

Hyeung-geun Park et al., *Bioorganic & Medicinal Chemistry Letters* 13 (2003) pp. 197-200, 601-604.

Modulation of Capsaicin-Induced Calcium Uptake Into Primary Cultured Rat Dorsal Root Ganglion Sensory Neurons and Characterization of Capsaicin-Hydrolyzing Enzyme Purified from Rat Liver, Feb. 1996.

Christopher S. J. Walpole et al., "The Discovery of Capsazepine, the First Competitive Antagonist of the Sensory Neuron Excitants Capsaicin and Resiniferatoxin," J. Med. Chem., vol. 37, No. 13, Jun. 24, 1994, pp. 1942-1954.

Gilles Klopman et al., "Quantitative structure-agonist activity relationship of capsaicin analogues," Journal of Computer-Aided Molecular Design, vol. 9, No. 3, (1995) pp. 283-294.

M. Hosseini et al., "Using Artificial Neural Networks to Classify the Activity of Capsaicin and its Analogues," J. Chem. Inf. Comput. Sci., vol. 37, No. 6, Nov. 1997, pp. 1129-1137.

Edward K. Dzladulewicz et al., "1-(2-Nitrophenyl)thiosemicarbazides: A Novel Class of Potent, Orally Active Non-Peptide Antagonist for the Bradykinin $B_2$ Receptor," J. Med. Chem. vol. 43, No. 5, Mar. 9, 200 pp. 769-771.

John F. Olin et al., "The Action of the Halogen Hydrins and of Ethylene Oxide on the Thioureas," Journal of the American Chemical Society, vol. 52, No. 8, Aug. 1930, pp. 3323-3327.

Charles Larsen et al., "Thermal Fragmentations VI. The Preparation of Aryl N-Monoalkydithiocarbamates and Their Behaviour upon Heating," ACTA Chemica Scandinavica, vol. 27, No. 6, Jun. 1973, pp. 2001-2012.

Zhen-Chu Chen et al., "Polyvalent Iodine in Synthesis. 2. A New Method for the Preparation of Aryl Esters of Dithlocarbamic Acids," Journal of Organic Chemistry, vol. 52, No. 18, Sep. 4, 1987, pp. 4117-4118.

Eugene Lieber et al., "Reaction of 5-Amino-1,2,3,4-Thiatriazole with Benzylamine," Journal of Organic Chemistry, vol. 22. No. 930, Sep. 1957, pp. 1054-1056.

J. Bourdais et al., "Polycyclic Azines. III. Synthesis of 3-Aminoimidazol[1,5-a]pyridine Derivatives by Cyclodesulphurization of $N^1$-Substituted-N-(2-Pyridylmethyl)thioureas with Dicyclohexylcarbodiimide (2,3)," Journal of Heterocyclic Chemistry, vol. 17, No. 5, May 1980, pp. 555-558.

Walter Ried et al., "2-Imino-1, 3-thiazetidine aus Thiohamstoffen mit intramolekularer Wasserstoffbrücke," Chemische Berichte, vol. 111, No. 1, Jan. 1978, pp. 143-154.

Wrigglesworth et al., "Analogues of Capsaicin with Agonist Activity as Novel Analgesic Agents: Structure—Activity Studies. 4. Potent, Orally Active Analgesics," J. Med Chem. 1996, 39 4942-4951.

McKay et al., "Bacteriostats. VI.[1a] Bacteriostatic Activities of Some Substituted Guanidines[1b]," Bacteriostats. VI, Sep., 1963, 587-595.

"Controlling Pain in the 21st Century," Report on the Society for Medicines Research Meeting Held at Charing Cross and Westminster Medical School, London, Jul. 10, 1997.

Chem Abstract Online printout of JP 11-35545, 1999, m=221070-38-3.

Jeewoo et al., "3-Acyloxy-2-phenalkylpropyl Amides and Esters of Homovanillic Acid as Novel Vanilloid Receptor Agonists," Bioorganic & Medicinal Chemistry Letters 9 (1999) 2909-2914.

K. D. Janda et al., "Antibody Catalysis of Bimolecular Amide Formation," J. Am. Chem. Soc. 1988, 110, 4835-4837.

Oh, Uhtaek, et al., "Capsaicin Activates a Nonselective Cation Channel in Cultured Neonatal Rat Dorsal Root Ganglion Neurons," *J. Neurosci.*, (16)5:1659-1667 (1996).

Accession No. (AN) 2004:429173 CHEMCATS, Jan. 1, 2004.

Accession No. (AN) 2003:2480724 CHEMCATS, Nov. 12, 2004.

\* cited by examiner

THIOUREA COMPOUNDS AND THE PHARMACEUTICAL COMPOSITIONS CONTAINING THE SAME

TECHNICAL FIELD

The present invention relates to thiourea compounds and the pharmaceutical compositions containing the same, and particularly, to thiourea compounds with superior efficacy as an antagonist against vanilloid receptor (VR) and the pharmaceutical compositions thereof.

BACKGROUND ART

As diseases associated with the activity of vanilloid receptor, pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma or chronic obstructive pulmonary disease, irritation of skin, eye or mucous membrane, fervescence, stomach-duodenal ulcer, inflammatory bowel disease and inflammatory diseases can be enumerated. The present invention provides pharmaceutical compositions for prevention or treatment of these diseases.

Yet, the diseases described above are only for enumeration, not to limit the scope of clinical application of vanilloid receptor antagonist.

Capsaicin (8-methyl-N-vanillyl-6-nonenamide) is a main pungent component in hot peppers. Hot peppers have been used, for a long time, not only as a spice but also as traditional medicine in the treatment of gastric disorders and when applied locally, for the relief of pain and inflammation (Szallasi and Blumberg, 1999, Pharm, Rev. 51, pp159–211). Capsaicin has a wide spectrum of biological actions, and not only exhibits effects on the cardiovascular and respiratory systems but also induces pain and irritancy on local application. Capsaicin, however, after such induction of pain, induces desensitization, both to capsaicin itself and also to other noxious stimuli to make the pain stopped. Based on this property, capsaicin and its analogues such as olvanil, nuvanil, DA-5018, SDZ-249482, resiniferatoxin are either used as analgesic agent, therapeutic agent for incontinentia urinae or skin disorder, or under development (Wriggleworth and Walpole, 1998, Drugs of the Future 23, pp 531–538).

Transmissions of mechanical, thermal and chemical noxious stimuli are mainly occurred by primary afferent nerve fibers of fine unmyelinated nerve (C-fiber) and thin myelinated nerve (A-fiber), and main reaction site of capsaicin and its analog called vanilloid is present at the nerve fiber transmitting the noxious stimuli. Capsaicin acts at the receptor existing on these neurons to induce potent stimuli by causing potent inflow of mono-and di-valent cations such as calcium and sodium, then exhibits potent analgesic effect by blocking the nervous function (Wood et al., 1988, J. Neurosci, 8, pp3208–3220). Vanilloid receptor (VR-1) has been recently cloned and its existence becomes clear(Caterina et al., 1997, Nature 389, pp816–824). It was clarified that this receptor transmits not only stimuli by capsaicin anlogues (vanilloid) but also various noxious stimuli such as proton and thermal stimuli (Tominaga et al., 1998, Neuron 21, pp531–543). Based on this, it is considered that vanilloid receptor functions as a integrative modulator against various noxious stimuli and carries out critical role in transmissions of pain and noxious stimuli. Recently, knock-out mouse in which gene encoding for vanilloid receptor was deleted was prepared (Caterina et al., 2000, Science 288, pp306–313; Davis et al., 2000, Nature 405, pp183–187). Compared to normal mice, the mouse was found out to exhibit much reduced reaction to thermal stimuli and thermal pain, while exhibiting no difference in general behavior, reconfirming the importance of the receptor in transmission of noxious signal. However, except proton, no other endogenous ligand, not exogenous ligand such as capsaicin, actually involved in transmission of noxious stimuli at vanilloid receptor was known. It is considered that leucotriene metabolite represented by 12-hydroperoxyeicosatetraenoic acid (12-HPETE) (Hwang et al., 2000, PNAS 11, pp6155–6160) and arachidonic aicd derivatives such as anandamide (Zygmunt et al., 2000, Trends Pharmocol. Sci. 21, pp43–44) act as the most likely endogenous ligand for the receptor and proton acts as a cofactor with receptor-stimulating activity, rather than as a direct ligand.

As such, a capsaicin-sensitive sensory nerve cell and a vanilloid receptor existing in the cell are distributed over the entire body and play basic function in transmission of noxious stimuli and pain, further act as crucial factor in expression of neurogenic inflammation, thereby to have close relation with the cause of neuropathies, nerve injury, stroke, asthma, chronic obstructive pulmonary diseases, urinary bladder hypersensitiveness, irritable bowel syndrome, inflammatory bowel disease, fervescence, skin disorder and inflammatory disease. Lately, their correlation even with neuropathic disease is suggested (WO 99/00125). Recently, attention has focused to the role of afferent sensory nerve responding to capsaicin in gastrointestinal injury, and it was proposed that the afferent nerve might have a dual character that it exhibits protective action against gastric damage by improving gastric microcirculation through releasing peripheral neuropeptide such as CGRP (calcitonin gene-related peptide), while inducing gastric injury by stimulating sympathetic nervous system (Ren et al., 2000, Dig. Dis. Sci. 45, pp830–836). It is determined that vanilloid receptor antagonist has very high potential to be used for prevention or treatment of the said various diseases by blocking the vanilloid receptor conducting such varied functions.

Though it may be, theoretically, anticipated that antagonist for this receptor would exhibit substantial degree of inhibitory action against pain and neurogenic inflammation, it was found out that the competitive antagonist for this receptor, capsazepine, almost the only one known until now, failed to exhibit significant analgesic and anti-inflammatory effects (Perkins and Campbell, 1992, Br. J. Pharmacol. 107, pp329–333). Therefore, not much progress was made on this field. However, recently, there has been a report on significant results for analgesic action of capsazepine in animal studies (Kwak et al., 1998, Neurosci. 86, pp619–626; Santos and calixto, 1997, Neurosci. Lett. 235, pp73–76), in particular, the inventors of the present invention clearly demonstrated through animal studies the analgesic and anti-inflammatory effects of the strong vanilloid receptor antagonists which were identified through experiments in laboratory, and based on this, strongly suggested the development potential of vanilloid receptor antagonist as an analgesic and anti-inflammatory agent. Yet, though the vanilloid receptor antagonist derived from the present studies will mainly act based on the antagonistic activity of itself, even a possibility that it could exhibit the pharmacological activity through transformation into agonist via metabolism after absorption into body is not to be excluded.

To resolve the problems described above, the present invention is to provide novel compounds which are selectively antagonistic to vanilloid receptor and exhibit analgesic and anti-inflammatory effects while causing no irritancy, and pharmaceutical compositions containing the same.

DISCLOSURE OF THE INVENTION

In order to attain the above objects, the present invention provides a novel compound of formula (I):

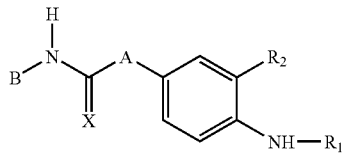

(I)

wherein

X represents a sulfur atom or an oxygen atom;

$R_1$ represents a lower alkyl sulfonyl group having 1 to 5 carbon atoms, an aryl sulfonyl group or a lower alkyl carbonyl group having 1 to 5 carbon atoms, which may be unsubstituted or substituted with a halogen atom;

$R_2$ represents a hydrogen atom, a methoxy group or a halogen atom;

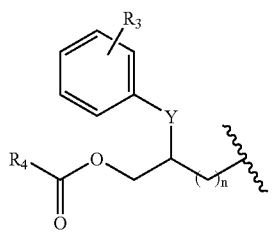

when A is —NHCH$_2$—, B represents wherein, n is 0 or 1, or when A is —CH$_2$—, R represents 4-t-butylbenzyl, 3,4-dimethylphenylethyl,

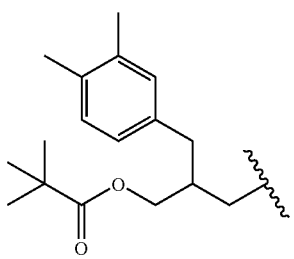

or an oleyl group;

$R_4$ represents a lower alkyl group having 1 to 5 carbon atoms or a phenyl group.

The present invention also provides a pharmaceutical composition comprising a compound of formula (I) or a pharmaceutically acceptable salt thereof as an active ingredient.

The compounds according to the present invention can chemically be synthesized by the following reaction schemes. However, these are given only for illustration of the invention and are not intended to limit to them.

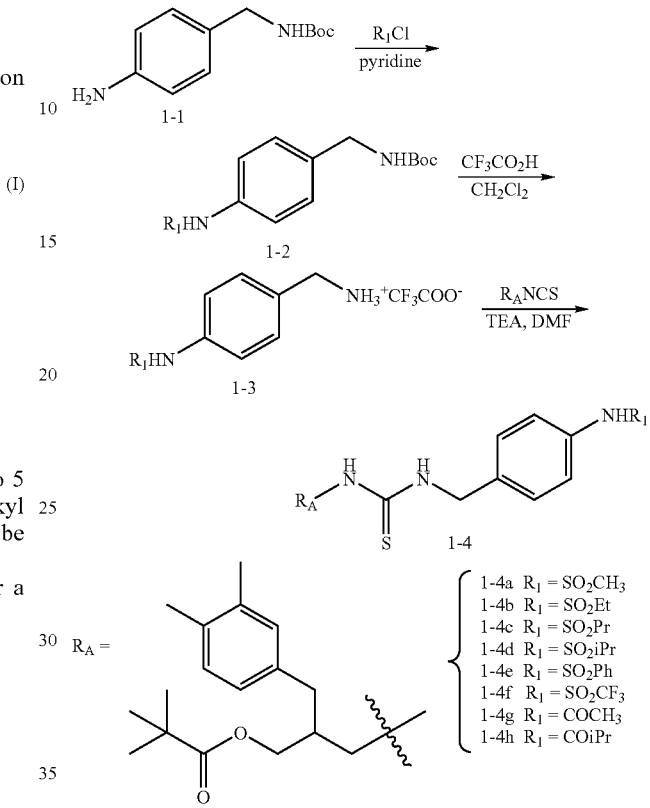

[SCHEME 1]

As depicted in the above Scheme 1, a compound 1-1 was synthesized by selectively protecting 4-aminobenzylamine with Boc(t-butoxycarbonyl) group. Amine of formula 1-1 was reacted with various kinds of agents, e.g., sulfonylchloride or acyl chloride to synthesize a compound 1-2, Boc group was removed from the compound 1-2 under acidic conditions, and then various kinds of isothiocyanate-based compounds were reacted therewith to prepare compounds 1-4a~1-4h.

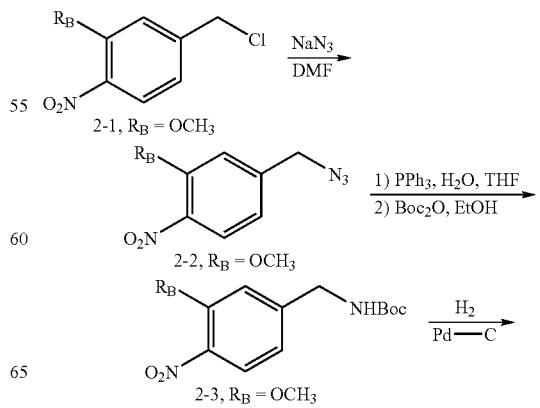

[SCHEME 2]

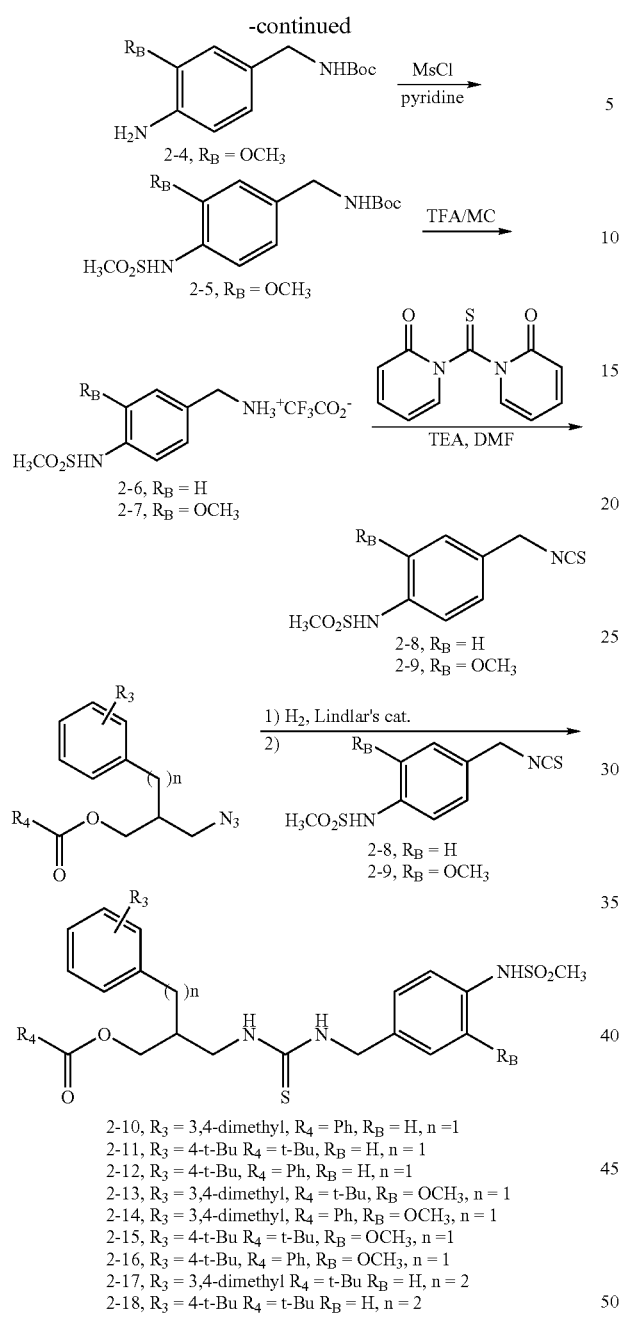

2-10, R₃ = 3,4-dimethyl, R₄ = Ph, R_B = H, n =1
2-11, R₃ = 4-t-Bu R₄ = t-Bu, R_B = H, n = 1
2-12, R₃ = 4-t-Bu, R₄ = Ph, R_B = H, n =1
2-13, R₃ = 3,4-dimethyl, R₄ = t-Bu, R_B = OCH₃, n = 1
2-14, R₃ = 3,4-dimethyl, R₄ = Ph, R_B = OCH₃, n = 1
2-15, R₃ = 4-t-Bu R₄ = t-Bu, R_B = OCH₃, n =1
2-16, R₃ = 4-t-Bu, R₄ = Ph, R_B = OCH₃, n = 1
2-17, R₃ = 3,4-dimethyl R₄ = t-Bu R_B = H, n = 2
2-18, R₃ = 4-t-Bu R₄ = t-Bu R_B = H, n = 2

As depicted in the above Scheme 2, azide group was introduced into 3-methoxy-4-nitrobenzyl chloride, reduced, and then protected with Boc group to synthesize a compound 2-3. Nitro group of the compound 2-3 was reduced to produce an amine compound 2-4, methanesulfonylamino group (mesyl group) was introduced thereinto to synthesize a compound 2-5, and then Boc group was removed therefrom to synthesize an amine compound 2-7. The amine compound 2-7 was treated with 1,1-thio-1H-carbonyl-di-2-pyridone to synthesize an isothiocyanate compound 2-9 as a main intermediate. The azide compounds previously prepared was reacted with the compound 2-9 to prepare compounds 2-13~2-16.

In case R_B is H, a compound 2-8 was synthesized in accordance with the above process except that 4-nitrobenzylchloride was used as a starting material, and the compound 2-8 was reacted with azide compound to produce compounds 2-10~2-12, 2-17 and 2-18.

[SCHEME 3]

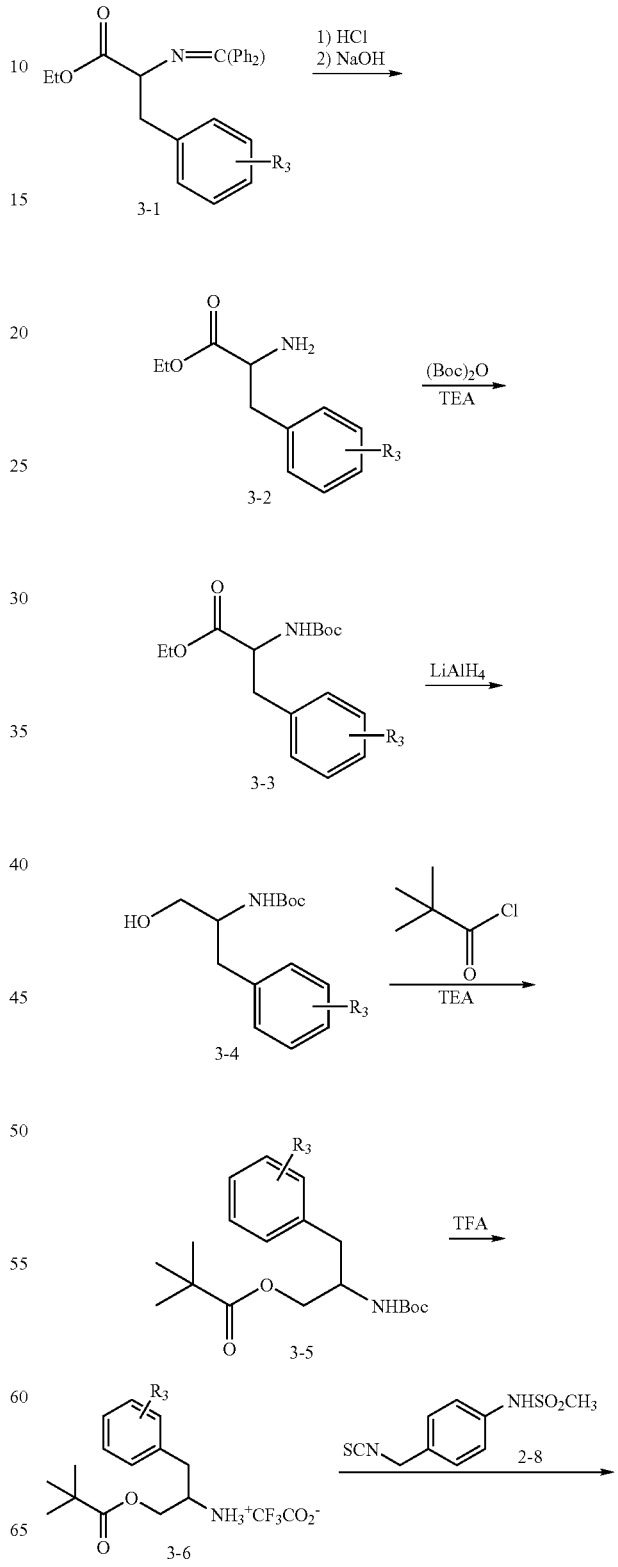

-continued

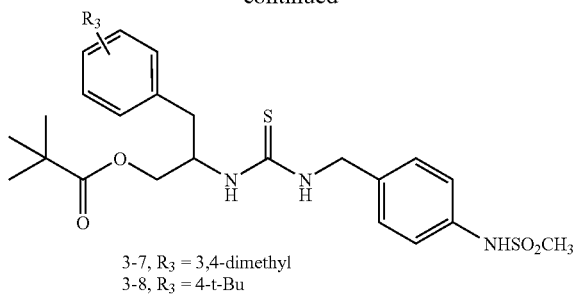

3-7, $R_3$ = 3,4-dimethyl
3-8, $R_3$ = 4-t-Bu

As depicted in the above Scheme 3, amine salt 3-6 was synthesized by using a compound 3-1 as a starting material according to a general method, and then the amine salt 3-6 was reacted with an isocyanate compound 2-8 to produce compounds 3-7 and 3-8.

[SCHEME 4]

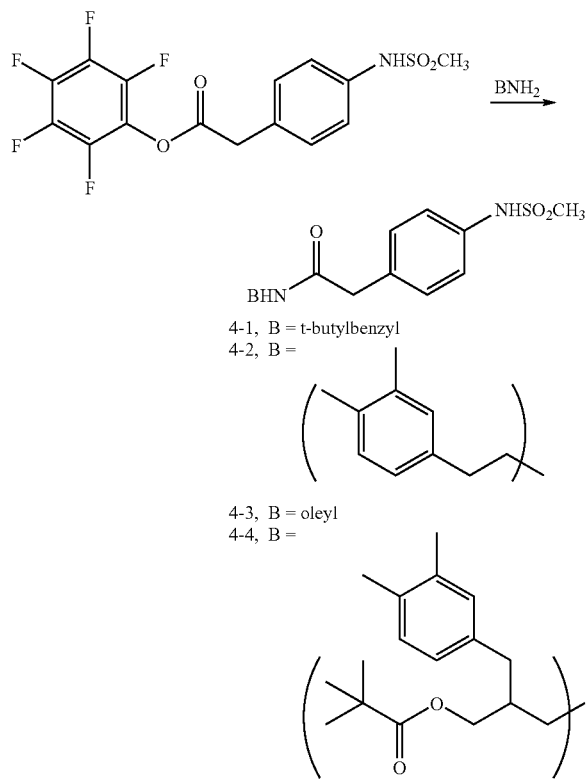

4-1, B = t-butylbenzyl
4-2, B =

4-3, B = oleyl
4-4, B =

Compounds 4-1~4-4 were produced by condensing pentafluorophenyl ester of 4-methanesulfonylaminophenylacetic acid with the known amines.

The compound of formula (1) according to the present invention can be provided as a pharmaceutical composition containing pharmaceutically acceptable carriers, adjuvants, or diluents. For instance, the compounds of the present invention can be dissolved in oils, propylene glycol or other solvents which are commonly used to produce an injection. Suitable examples of the carriers include, physiological saline, polyethylene glycol, ethanol, vegetable oils, isopropyl myristate, etc., but are not limited to them. For topical administration, the compounds of the present invention can be formulated in the form of ointments and creams.

The pharmaceutical composition containing the compound of the present invention as an active ingredient can be used for treating acute, chronic, inflammatory or neuropathic pains; treating urinary bladder hypersensitiveness or irritable bowel syndrome (IBS); treating asthma; preventing or treating neurodegenerative diseases; or preventing or treating neurotic skin disorder, or irritation of skin, eye or mucous membrane.

Hereinafter, the formulating methods and kinds of excipients will be described, but the present invention is not limited to them.

The compound according to the present invention may also be used in the forms of pharmaceutically acceptable salts thereof, and may be used either alone or in combination or in admixture with other pharmaceutically active compounds.

The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

The preferable dose level of the compounds according to the present invention depends upon a variety of factors including the condition and body weight of the patient, severity of the particular disease, dosage form, and route and period of administration, but may appropriately be chosen by those skilled in the art. The compounds of the present invention are preferably administered in an amount ranging from 0.001 to 100 mg/kg of body weight per day, and more preferably from 0.01 to 30 mg/kg of body weight per day. Doses are administered from once to several portions per day. The compounds of the present invention must be present in a pharmaceutical composition in an amount of 0.0001~10% by weight, and preferably 0.001~1% by weight, based on the total amount of the composition.

The pharmaceutical composition of the present invention can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

BEST MODE FOR CARRYING OUT THE INVENTION

The present invention is more specifically explained by the following examples. However, it should be understood that the present invention is not limited to these examples in any manner.

EXAMPLES 1~8

The Examples 1~8 are divided into three steps (step 1, 2 and 3), and the general methods for synthesizing the respective compounds are as follows.

Step 1: General Method for Synthesizing Compound (1-2)

Compound 1-1 (5.3 mmol) was dissolved in pyridine (10 mL), cooled to 0° C., and then acyl chloride (6.34 mmol) was slowly added thereto. The resulting reaction mixture was stirred at room temperature for 24 hours. The mixture was neutralized with aqueous 1M hydrochloric acid, diluted with water, and then extracted several times with dichloromethane. The extracted organic layers were collected, washed successively with water and saturated aqueous sodium chloride solution, dried over anhydrous magnesium sulfate, and then concentrated under reduced pressure. The resulting residue was purified by column chromatography (eluent: hexane/ethyl acetate=1/1) to yield the title compound 1-2.

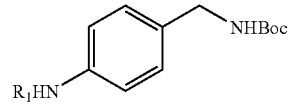

1-2

| Example-step | Compound No. | $R_1$ | Spectral data |
|---|---|---|---|
| 1-1 | 1-2a | $SO_2CH_3$ | $^1$H NMR(300 MHz, CDCl$_3$): δ 7.1–7.3 (m, 4H), 6.77 (s, 1H), 4.88 (bs, 1H), 4.28 (d, 2H), 2.99 (s, 3H), 1.46 (s, 9H) |
| 2-1 | 1-2b | $SO_2Et$ | $^1$H NMR(300 MHz, CDCl$_3$): δ 7.1–7.3 (m, 4H), 6.80 (s, 1H), 4.88 (bs, 1H), 4.25 (d, 2H), 3.07 (q, 3H), 1.46 (s, 9H), 1.36 (t, 3H) |
| 3-1 | 1-2c | $SO_2Pr$ | $^1$H NMR(300 MHz, CDCl$_3$): δ 7.23 (dd, 4H), 6.85 (s, 1H), 4.89 (bs, 1H), 4.28 (d, 2H), 3.05 (m, 2H), 1.67 (m, 2H), 1.46 (s, 9H), 1.01 (t, 3H) |
| 4-1 | 1-2d | $SO_2iPr$ | $^1$H NMR(300 MHz, CDCl$_3$): δ 7.17–7.31 (m, 4H), 6.98 (s, 1H), 4.87 (bs, 1H), 4.28 (d, 2H), 3.28 (m, 1H), 1.3–1.5 (m, 15H) |
| 5-1 | 1-2e | $SO_2Ph$ | $^1$H NMR(300 MHz, CDCl$_3$): δ 7.75 (d, 2H), 7.54 (m, 3H), 7.15 (d, 2H), 7.02 (d, 2H), 6.68 (s, 1H), 4.80 (t, 1H), 4.23 (d, 2H), 1.44 (s, 9H) |
| 6-1 | 1-2f | $SO_2CF_3$ | $^1$H NMR(300 MHz, CDCl$_3$): δ 7.2–7.4 (m, 4H), 6.68 (s, 1H), 4.21 (d, 2H), 1.37 (s, 9H) |
| 7-1 | 1-2g | $COCH_3$ | $^1$H NMR(300 MHz, CDCl$_3$): δ 7.46 (d, 2H), 7.24 (d, 2H), 4.80 (bs, 1H), 4.27 (d, 2H), 2.17 (s, 3H), 1.45 (s, 9H) |
| 8-1 | 1-2h | COiPr | $^1$H NMR(300 MHz, CDCl$_3$): δ 7.50 (d, 2H), 7.24 (d, 2H), 7.11 (bs, 1H), 4.78 (bs, 1H), 4.25 (d, 2H), 2.50 (m, 1H), 1.45 (s, 9H), 1.24 (d, 6H) |

Step 2: General Method for Synthesizing Compound (1-3)

Compound 1-2 (4.8 mmol) was dissolved in dichloromethane (20 mL), cooled to 0° C., and trifluoroacetic acid (5 mL) was slowly added thereto. The resulting mixture was stirred at 0° C. for an hour and 30 minutes. The solvent was evaporated under reduced pressure to obtain a flame-colored residue. The obtained residue was washed with ethyl ether and filtered to yield the title compound 1-3.

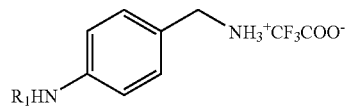

1-3

| Example-step | Compound No. | $R_1$ | Spectral data |
|---|---|---|---|
| 1-2 | 1-3a | $SO_2CH_3$ | $^1$H NMR(300 MHz, DMSO): δ 8.14 (bs, 3H), 7.39 (d, 2H), 7.22 (d, 2H), 3.97 (s, 2H), 2.99 (s, 3H) |
| 2-2 | 1-3b | $SO_2Et$ | $^1$H NMR(300 MHz, DMSO): δ 8.09 (bs, 3H), 7.51 (d, 2H), 7.33 (d, 2H), 4.01 (s, 2H), 2.79 (q, 2H), 1.46 (t, 3H) |
| 3-2 | 1-3c | $SO_2Pr$ | $^1$H NMR(300 MHz, DMSO): δ 7.69 (d, 2H), 7.35 (d, 2H), 4.03 (s, 2H) 2.76 (t, 2H), 1.92 (m, 2H), 1.05 (t, 3H) |
| 4-2 | 1-3d | $SO_2iPr$ | $^1$H NMR(300 MHz, DMSO): δ 7.82 (d, 2H), 7.37 (d, 2H), 3.99 (s, 2H) 3.53 (m, 1H), 1.53 (d, 6H) |

-continued

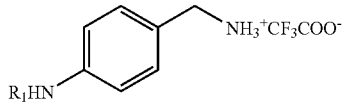

1-3

| Example-step | Compound No. | R₁ | Spectral data |
|---|---|---|---|
| 5-2 | 1-3e | SO₂Ph | $^1$H NMR(300 MHz, DMSO): δ 8.17 (d, 2H), 7.89 (d, 2H), 7.4–7.6 (m, 3H), 4.03 (s, 2H) |
| 6-2 | 1-3f | SO₂CF₃ | $^1$H NMR(300 MHz, DMSO): δ 7.9 (bs, 3H), 7.1–7.3 (m, 4H), 4.00 (bs, 2H) |
| 7-2 | 1-3g | COCH₃ | $^1$H NMR(300 MHz, CDCl₃): δ 7.49 (m, 4H), 4.17 (s, 2H), 2.18 (s, 3H) |
| 8-2 | 1-3h | COiPr | $^1$H NMR(300 MHz, CDCl₃): δ 7.50 (m, 4H), 4.17 (s, 2H), 2.70 (m, 1H), 1.22 (d, 6H) |

Step 3: General Method for Synthesizing Compound (1-4)

The compound 1-3 (0.38 mmol) was dissolved in DMF (1 mL), and triethylamine (0.38 mmol) was added thereto. The mixture was stirred at room temperature under nitrogen for 1 hour. To the mixture was added 2,2-dimethyl-propionic acid 3-(3,4-dimethylphenyl)-2-isothiocyanatomethylpropyl ester (0.38 mmol), and the resulting mixture was stirred for 24 hours. The reaction mixture was diluted with water, extracted several times with ethyl acetate. The collected organic layer was washed successively with water and saturated aqueous sodium chloride solution, dried over anhydrous magnesium sulfate, and concentrated under reduced pressure to obtain a residue. The obtained residue was purified by column chromatography (eluent: hexane/ethyl acetate=3/2) to yield the compound 1-4.

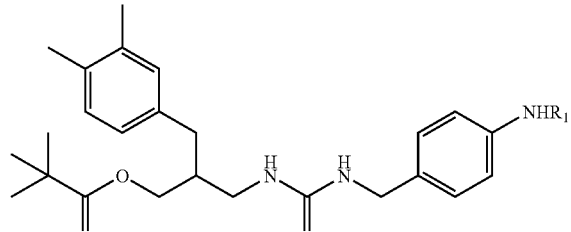

1-4

| Example-step | Compound No. | R₁ | Spectral data |
|---|---|---|---|
| 1-3 | 1-4a | SO₂CH₃ | $^1$H NMR(300 MHz, CDCl₃): δ 7.28 (d, 2H), 7.17 (d, 2H), 6.8–7.1 (m, 3H), 6.68 (s, 1H), 6.34 (m, 1H), 6.09 (brs, 1H), 4.51 (bs, 2H), 4.17 (m, 1H), 3.79 (m, 2H), 3.22 (m, 1H), 2.99 (s, 3H), 2.5–2.7 (m, 2H), 2.2–2.3 (m, 7H), 1.23 (s, 9H); mp = 60° C. |
| 2-3 | 1-4b | SO₂Et | $^1$H NMR(300 MHz, CDCl₃): δ 7.25 (d, 2H), 7.16 (d, 2H), 6.8–7.1 (m, 3H), 6.40 (m, 1H), 6.21 (bs, 1H), 4.50 (brs, 2H), 4.15 (m, 1H), 3.78 (m, 2H), 3.24 (m, 1H), 3.08 (q, 3H), 2.5–2.7 (m, 2H), 2.2–2.3 (m, 7H), 1.24 (s, 9H); mp = 48° C. |
| 3-3 | 1-4c | SO₂Pr | $^1$H NMR(300 MHz, CDCl₃): δ 7.25 (d, 2H), 7.14 (d, 2H), 6.8–7.1 (m, 3H), 6.45 (bs, 1H), 6.30 (brs, 1H), 4.51 (brs, 2H), 4.15 (m, 1H), 3.81 (m, 2H), 3.24 (m, 1H), 3.03 (t, 2H), 2.5–2.7 (m, 2H), 2.23 (m, 7H), 1.83 (q, 2H), 1.24 (s, 9H), 1.00 (t, 3H); mp = 54° C. |
| 4-3 | 1-4d | SO₂iPr | $^1$H NMR(300 MHz, CDCl₃): δ 7.1–7.3 (m, 4H), 6.8–7.0 (m, 3H), 6.48 (m, 2H), 4.50 (brs, 2H), 4.13 (m, 1H), 3.80 (m, 2H), 3.25 (m, 2H), 2.5–2.7 (m, 2H), 2.25 (m, 7H), 1.34 (d, 6H), 1.23 (s, 9H); mp = 48° C. |
| 5-3 | 1-4e | SO₂Ph | $^1$H NMR(300 MHz, CDCl₃): δ 7.76 (d, 2H), 7.52 (m, 2H), 6.8–7.1 (m, 3H), 6.41 (bs, 2H), 6.19 (brs, 2H), 4.43 (brs, 2H), 4.12 (m, 1H), 3.78 (m, 2H), 3.21 (m, 1H), 2.5–2.7 (m, 2H), 2.23 (m, 7H), 1.23 (s, 9H); mp = 66° C. |

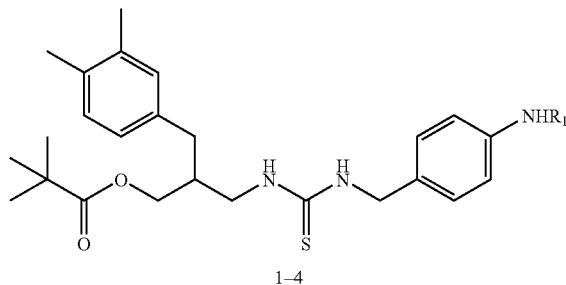
1-4
| Example-step | Compound No. | R₁ | Spectral data |
|---|---|---|---|
| 6-3 | 1-4f | SO₂CF₃ | ¹H NMR(300 MHz, CDCl₃): δ 7.28 (d, 2H), 7.17 (d, 2H), 6.8–7.1 (m, 3H), 6.48 (brs, 1H), 6.36 (brs, 1H), 4.50 (brs, 2H), 4.15 (m, 1H), 3.75 (m, 2H), 3.28 (m, 1H), 2.58 (m, 2H), 2.11–2.24 (m, 7H), 1.23 (s, 9H); mp = 44° C. |
| 7-3 | 1-4g | COCH₃ | ¹H NMR(300 MHz, CDCl₃): δ 7.46 (d, 2H), 7.24 (d, 2H), 6.9 (m, 3H), 6.28 (brs, 1H), 6.07 (brs, 1H), 4.43 (bs, 2H), 4.13 (m, 1H), 3.75 (m, 2H), 3.27 (m, 1H), 2.54 (m, 2H), 2.21 (m, 10H), 1.22 (s, 9H) |
| 8-3 | 1-4h | COiPr | ¹H NMR(300 MHz, CDCl₃): δ 7.51 (d, 2H), 7.22 (m, 2H), 6.93 (m, 3H), 6.28 (brs, 1H), 6.07 (brs, 1H), 4.41 (brs, 2H), 4.13 (m, 1H), 3.74 (m, 2H), 3.27 (m, 1H), 2.52 (m, 3H), 2.21 (m, 7H), 1.24 (m, 15H) |
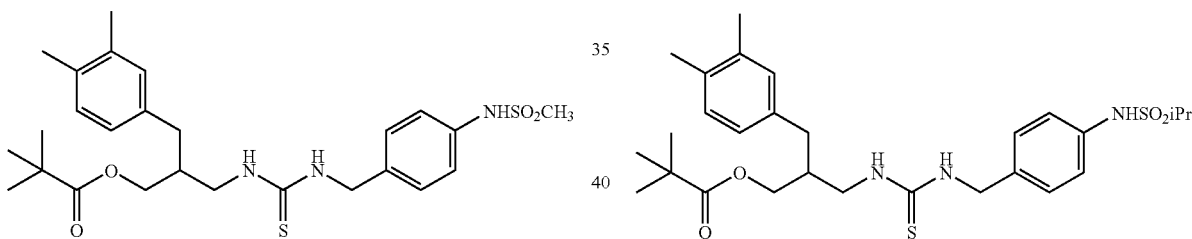
1-4a, 1-4d
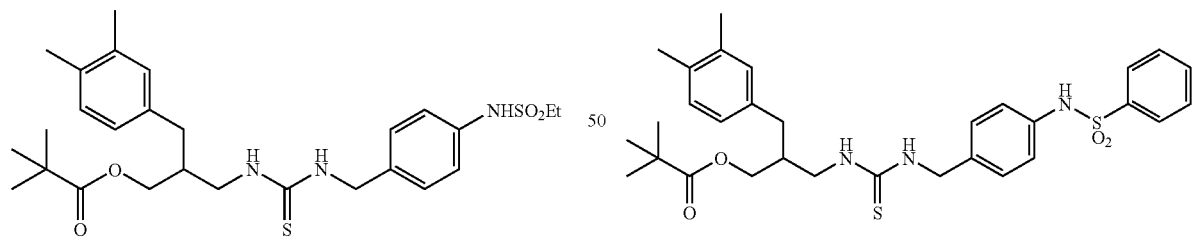
1-4b, 1-4e
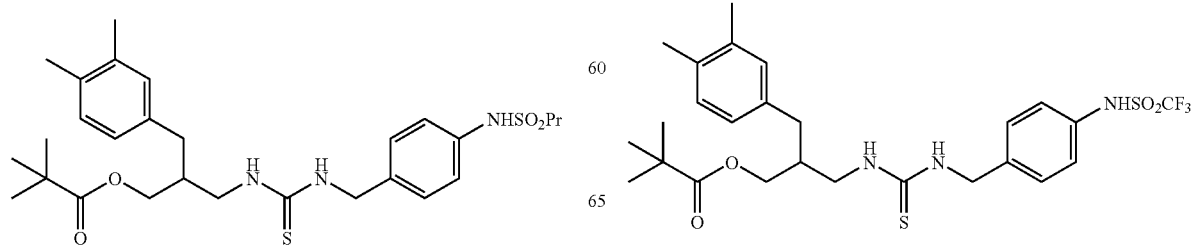
1-4c, 1-4f 1-4g

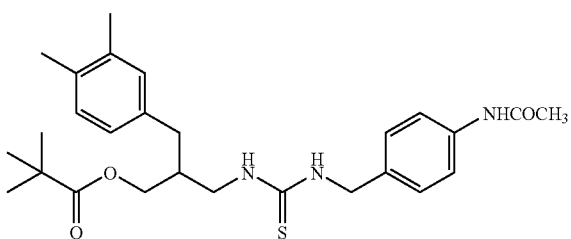

1-4h

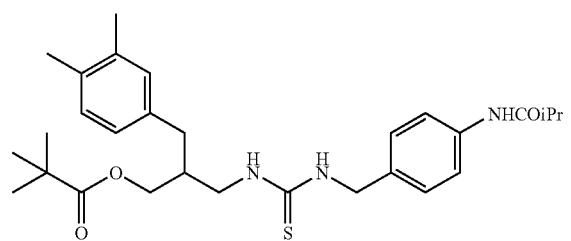

EXAMPLES 9~17

Step 1: Synthesis of 4-chloromethyl-2-methoxy-1-nitrobenzene-(2-1)

(3-methoxy-4-nitrophenyl)methanol (4.43 mmol) was dissolved in dichloromethane (10 mL), and then triethylamine (13.3 mmol) was added thereto. After the reaction mixture was cooled to 0° C., methanesulfonyl chloride (6.64 mmol) was slowly added thereto. The resulting mixture was stirred at room temperature under nitrogen for 24 hours. To the mixture was added ammonium chloride solution to terminate the reaction, diluted with water, and then extracted several times with dichloromethane. The collected organic layer was washed with water and brine, dried over anhydrous magnesium sulfate, and concentrated under reduced pressure. The resulting residue thus obtained was purified by column chromatography (eluent: hexane/ethyl acetate=4/1) to yield the title compound 2-1 (yield: 93%) as a yellow solid.

$^1$H NMR (CDCl$_3$) δ7.86 (d, 1H), 7.05 (s, 1H), 6.98 (d, 1H), 4.56 (s, 2H), 3.99 (s, 3H)

Step 2: Synthesis of 4-azidomethyl-2-methoxy-1-nitro-benzene (2-2)

A solution of the compound 2-1 (4.12 mmol) and sodium azide (16.5 mmol) in dimethylformamide (3 mL) was stirred at room temperature under nitrogen for 1 hour. The reaction mixture was diluted with water, extracted several times with ethyl acetate, and then the organic layer was collected. The collected organic layer was washed successively with water and saturated aqueous sodium chloride solution, dried over anhydrous magnesium sulfate, and concentrated under reduced pressure. The resulting residue was purified by column chromatography (eluent: hexane/ethyl acetate=3/1) to yield the title compound 2-2 (yield: 95%) as a yellow solid.

$^1$H NMR (CDCl$_3$) δ 7.87 (d, 1H), 7.05 (s, 1H), 6.99 (d, 1H), 4.45 (s, 2H), 3.99 (s, 3H)

Step 3: Synthesis of (3-methoxy-4-nitro-benzyl)-carbamic acid t-butyl ester (2-3)

A solution of the compound 2-2 (3.91 mmol), triphenyl phosphine (7.83 mmol) and water (7.83 mmol) in THF (30 mL) was stirred at room temperature for 24 hours. The reaction mixture was concentrated under reduced pressure. The residue thus obtained was dissolved in ethanol (20 mL), and Boc$_2$O (1.71 g) was added thereto. The resulting mixture was stirred at room temperature for 2 hours. After the reaction mixture was concentrated under reduced pressure, the resulting residue was purified by column chromatography (eluent: hexane/ethyl acetate=2/1) to yield the title compound 2-3 (yield: 86%) as a yellow liquid.

$^1$H NMR (CDCl$_3$)) δ 7.83 (d, 1H), 7.02 (s, 1H), 6.93 (d, 1H), 5.01 (brs, 1H), 4.35 (d, 2H), 3.95 (s, 3H), 1.47 (s, 9H)

Step 4: Synthesis of (4-amino-3-methoxybenzyl)carbamic acid t-butyl ester (2-4)

The compound 2-3 (3.13 mmol) was dissolved in methanol (20 mL), and then 10% palladium/carbon catalyst (85 mg) was added thereto. The resulting mixture was stirred at room temperature under hydrogen for 1 hour. After the reaction mixture was filtered, the filtrate was concentrated under reduced pressure to yield the title compound 2-4 (yield: 90%) as a brown liquid.

$^1$H NMR (CDCl$_3$) δ 6.6–6.7 (m, 3H), 4.19 (d, 2H), 3.88 (s, 3H), 1.46 (s, 9H)

Step 5: Synthesis of (4-methanesulfonylamino-3-methoxybenzyl)carbamic acid t-butyl ester (2-5)

The title compound 2-5 was obtained as a pink solid in a yield of 67% according to the same procedure as synthesizing method of compound 1-2a, except that the compound 2-4 (3.13 mmol) was used as a starting material.

$^1$H NMR (CDCl$_3$) δ 7.47 (d, 1H), 6.86 (m, 2H), 6.74 (s, 1H), 4.88 (bs, 1H), 3.88 (s,9H) 3H), 2.94 (s, 3H), 1.47 (s, 9H)

Step 6: Synthesis of 4-methanesulfonylamino-3-methoxybenzylammonium trifluoroacetate (2-7)

The title compound 2-7 was obtained as a green solid in a yield of 87% according to the same procedure as synthesizing method of compound 1-3a, except that the compound 2-5 (2.1 mmol) was used as a starting material.

$^1$H NMR (DMSO) δ 8.16 (bs, 3M), 7.29 (d, 1H), 7.20 (s, 1H), 6.99 (d, 1H),4.00 (s, 2H), 3.82 (s, 3H), 2.95 (s, 3H)

Step 7: General Method for Synthesizing Compounds (2-8 and 2-9)

The compound 2-6 or 2-7 (12 mmol) was dissolved in DMF (1 mL), and then triethylamine (12 mmol) was added thereto. The resulting mixture was stirred at room temperature under nitrogen for 1 hour. To the mixture was added 1,1-thio-1H-2-carbonyl-di-2-pyridone (12 mmol), and stirred for 24 hours. The reaction mixture was diluted with water, extracted several times with ethyl acetate, and then the organic layer was collected. The collected organic layer was washed with water and then with saturated aqueous sodium chloride solution, dried over anhydrous magnesium sulfate, and concentrated under reduced pressure. The resulting residue was purified by column chromatography (eluent: hexane/ethyl acetate=3/2) to yield the title compounds 2-8 or 2-9.

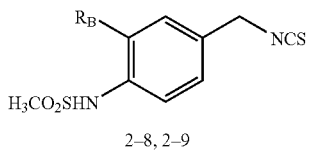

2–8, 2–9

| Compound No. | $R_B$ | Spectral data |
|---|---|---|
| 2-8 | H | $^1$H NMR(300 MHz, CDCl$_3$): δ 7.32 (d, 2H) 7.25 (d, 2H), 6.62 (s, 1H), 4.70 (s, 2H) 3.04 (s, 3H) |

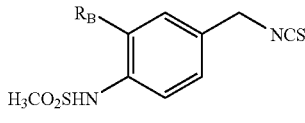

2–8, 2–9

| Compound No. | $R_B$ | Spectral data |
|---|---|---|
| 2-9 | OCH$_3$ | $^1$H NMR(300 MHz, CDCl$_3$): δ 7.29 (s, 1H) 6.96 (m, 2H), 5.09 (s, 2H), 3.82 (s, 3H), 3.04 (s, 3H) |

Step 8: General Method for Synthesizing Compounds (2-10~2-18)

A solution of azide compound (0.5 mmol) prepared in accordance with the well-known method, Lindlers catalyst (50 mmol) and the compound 2-8 in ethanol (5 mL) was subjected to hydrogenization reaction under hydrogen atmosphere for 2 hours. After the reaction mixture was filtered, the filtrate was concentrated under reduced pressure. The concentrate was purified by column chromatography (eluent: ethyl acetate/hexane=1/1) to yield the title compounds 2-10~2-18

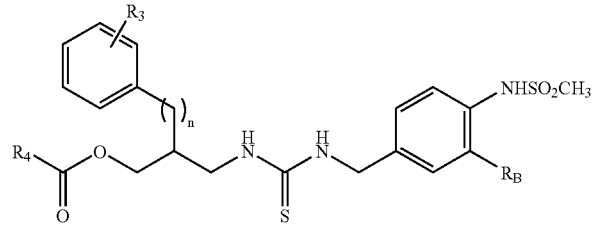

2–10~2–18

| Examples | Compound No. | R | Spectral data |
|---|---|---|---|
| 9 | 2-10 | $R_B$ = H<br>$R_3$ = 3,4-di-Me<br>$R_4$ = Ph<br>n = 1 | $^1$H NMR(300 MHz, CDCl$_3$): δ 8.01 (m, 2H), 7.4–7.6 (m, 3H), 7.1–7.3 (m, 4H), 6.9–7.0 (m, 3H), 6.53 (m, 1H), 6.40 (brs, 1H); 4.52 (brs, 2H), 4.35 (m, 1H), 4.17 (m, 1H), 3.82 (m, 1H), 3.41 (m, 1H), 2.93 (s, 3H), 2.5–2.7 (m, 2H), 2.1–2.3 (m, 7H); mp = 46° C. |
| 10 | 2-11 | $R_B$ = H<br>$R_3$ = 4-t-Bu<br>$R_4$ = t-Bu<br>n = 1 | $^1$H NMR(300 MHz, CDCl$_3$): δ 7.31 (d, 4H), 7.18 (d, 2H), 7.10 (d, 2H), 6.51 (s, 1H), 6.33 (t, 1H), 6.03 (brs, 1H), 4.53 (brs, 2H), 4.15 (m, 1H), 3.82 (m, 2H), 3.23 (m, 1H), 2.99 (s, 3H), 2.60 (t, 2H), 2.32 (m, 1H), 1.25 (d, 18H); mp = 61° C. |
| 11 | 2-12 | $R_B$ = H<br>$R_3$ = 4-t-Bu<br>$R_4$ = Ph<br>n = 1 | $^1$H NMR(300 MHz, CDCl$_3$): δ 8.01 (d, 2H), 7.4–7.6 (m, 3H), 7.1–7.3 (m, 4H), 6.54 (s, 1H), 6.39 (t, 1H), 6.10 (brs, 1H), 4.53 (brs, 2H), 4.39 (m, 1H), 4.07 (m, 1H), 3.82 (m, 1H), 3.38 (m, 1H), 2.97 (s, 3H), 2.68 (t, 2H), 2.48 (m, 1H, CH), 1.29 (s, 9H); mp = 68° C. |
| 12 | 2-13 | $R_B$ = OMe<br>$R_3$ = 3,4-di-Me<br>$R_4$ = t-Bu<br>n = 1 | $^1$H NMR(300 MHz, CDCl$_3$): δ 7.48 (d, 2H), 6.9–7.1 (m, 5H), 6.77 (s, 1H), 6.31 (m, 1H), 5.99 (brs, 1H), 4.49 (bs, 2H), 4.20 (m, 1H), 3.88 (s, 3H), 3.85 (m, 2H), 3.22 (m, 1H), 2.93 (s, 3H), 2.56 (m, 2H), 2.2–2.3 (m, 7H), 1.23 (s, 9H); mp = 49° C. |
| 13 | 2-14 | $R_B$ = OMe<br>$R_3$ = 3,4-di-Me<br>$R_4$ = Ph<br>n = 1 | $^1$H NMR(300 MHz, CDCl$_3$): δ 8.02 (t, 2H), 7.4–7.6 (m, 3H), 6.9–7.1 (m, 3H), 6.77 (s, 1H), 6.38 (m, 1H), 6.09 (bs, 1H), 4.45 (m, 1H), 4.05 (m, 1H) 3.85 (s, 3H), 3.37 (m, 1H), 2.92 (s, 3H), 2.67 (m, 2H), 2.43 (m, 1H), 2.25 (m, 6H); mp = 62° C. |
| 14 | 2-15 | $R_B$ = OMe<br>$R_3$ = 4-t-Me<br>$R_4$ = t-Bu | $^1$H NMR(300 MHz, CDCl$_3$): δ 7.45 (d, 2H), 7.30 (d, 2H), 7.08 (d, 2H), 6.8–7.0 (m, 3H), 6.39 (t, 1H), 6.24 (bs, 1H), 4.52 (bs, 2H), 4.15 (m, 1H), 3.82 (m, 5H), |

-continued

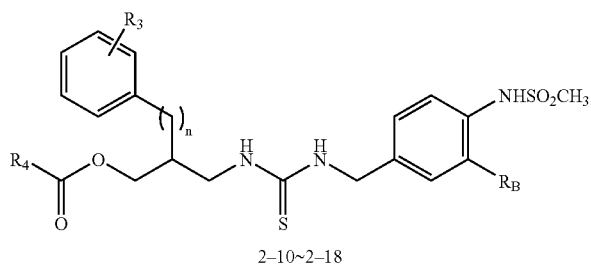

2-10~2-18

| Examples | Compound No. | R | Spectral data |
|---|---|---|---|
| | | n = 1 | 3.25 (m, 1H) 2.93 (s, 3H), 2.60 (m, 2H), 2.31 (m, 1H), 1.25 (d, 18H); mp = 62° C. |
| 15 | 2-16 | R$_B$ = OMe<br>R$_3$ = 4-t-Bu<br>R$_4$ = Ph | $^1$H NMR(300 MHz, CDCl$_3$): δ 8.03 (d, 2H), 7.4–7.6 (m, 3H), 7.1–7.3 (m. 4H), 6.77 (s, 1H), 6.38 (t, 1H), 6.10 (bs, 1H), 4.51 (bs, 2H), 4.43 (m, 1H), 4.08 (m, 1H), 3.82 (m, 4H), 3.38 (m, 1H), 2.92 (s, 3H), 2.69 (t, 2H), 2.36 (m, 1H), 1.29 (s, 9H); mp = 57° C. |
| 16 | 2-17 | n = 1<br>R$_B$ = H<br>R$_3$ = 3,4-di-Me<br>R$_4$ = t-Bu | $^1$H NMR(300 MHz, CDCl$_3$): δ 7.1–7.3 (m, 7H), 6.39 (t, 1H), 6.06 (bs, 1H), 4.59 (d, 2H), 4.16 (m, 1H), 3.97 (m, 1H) 3.77 (m, 2H), 3.22 (m, 1H), 2.99 (s, 3H), 2.68 (t, 2H), 2.05 (m, 1H), 1.58 (m, 2H), 1.25 (d, 9H) |
| 17 | 2-18 | n = 2<br>R$_B$ = H<br>R$_3$ = 4-t-Bu<br>R$_4$ = t-Bu | $^1$H NMR(300 MHz, CDCl$_3$): δ 7.33 (d, 2H), 7.17 (d, 2H), 6.9–7.1 (m, 3H), 6.42 (s, 1H), 6.36 (t, 1H), 6.06 (bs, 1H), 4.59 (d, 2H), 4.21 (m, 1H), 3.97 (m, 1H) 3.72 (m, 1H), 3.22 (m, 2H), 2.99 (s, 3H), 2.65 (t, 2H), 2.23 (m, 7H), 1.60 (m, 2H), 1.23 (s, 9H) |

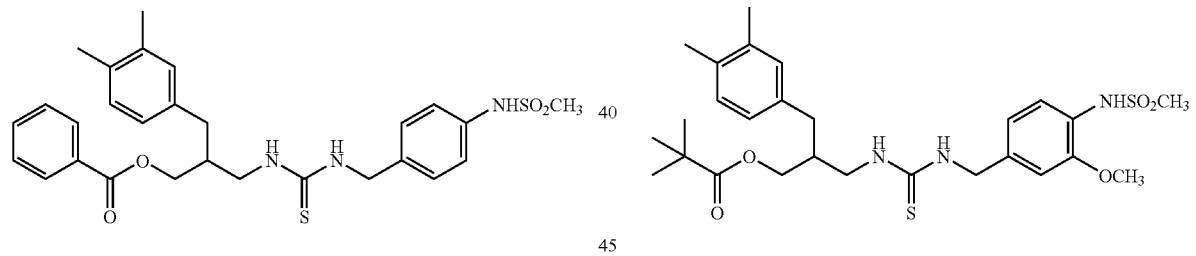

-continued

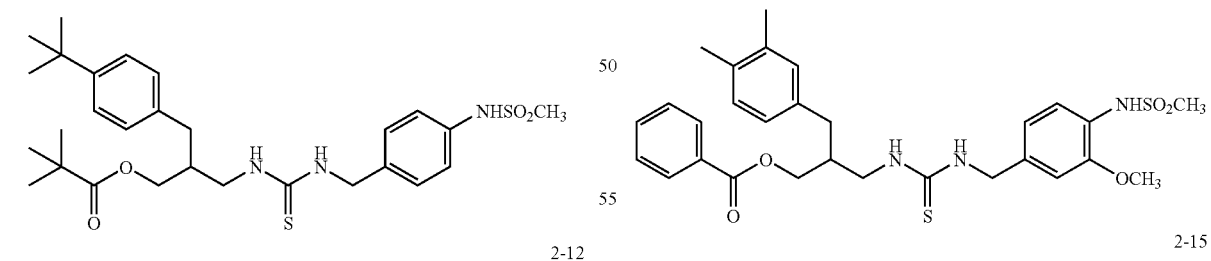

-continued

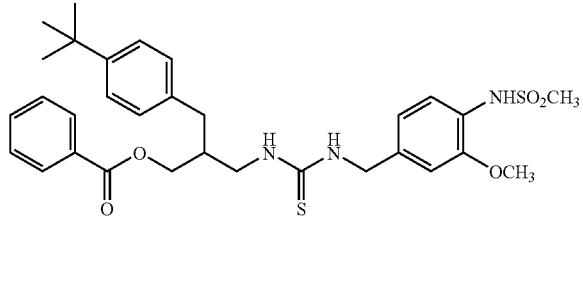
2-16

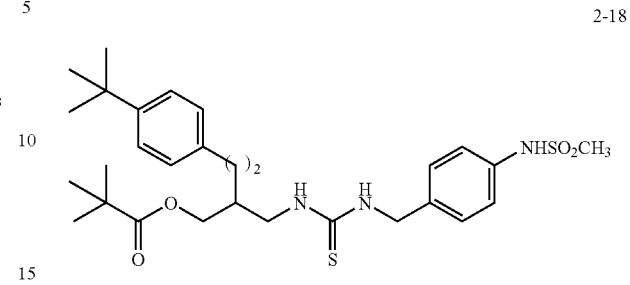
2-18

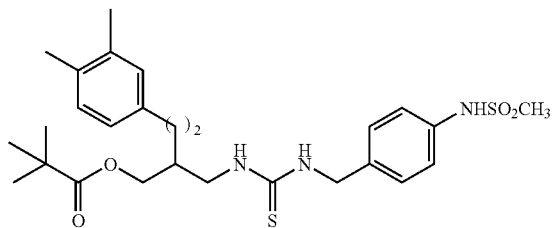
2-17

EXAMPLES 18~19

Step 1: General Method for Synthesizing Compound (3-1)

N-(diphenylmethyleneglycine)ethyl ester (1.83 mmol) was dissolved in dichloromethane (5 mL), and then 50% aqueous sodium hydroxide solution (3.66 mmol), tetrabutylammonium bromide (1.83 mmol) and alkyl halide (2.50 mmol) were added thereto. The reaction mixture was stirred at room temperature for 24 hours, neutralized with 6N aqueous hydrochloric acid, diluted with water, and then extracted several times with dichloromethane. After the obtained organic layer was dried over anhydrous magnesium sulfate and filtered, the filtrate was concentrated under reduced pressure. The concentrate was purified by column-chromatography (eluent: hexane/ethyl acetate=10/1) to yield the title compound 3-1.

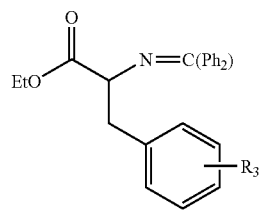

3-1

| Example-step | Compound No. | $R_3$ | Spectral data |
|---|---|---|---|
| 18-1 | 3-1a | 3,4-di-Me | $^1$H NMR(300 MHz, CDCl$_3$): δ 7.59 (t, 2H), 7.2–7.4 (m, 10H), 6.95 (m, 1H), 4.16–4.28 (m, 3H), 3.35 (dd, 1H), 3.17 (m, 1H), 2.12 (m, 6H), 1.23 (q, 3H) |
| 19-1 | 3-1b | 4-t-Bu | $^1$H NMR(300 MHz, CDCl$_3$): δ 7.59 (d, 2H), 7.2–7.4 (m, 10H), 6.95 (d, 2H), 4.11–4.24 (m, 3H), 3.1–3.3 (m, 2H), 1.25 (m, 12H) |

Step 2: General Method for Synthesizing Compound (3-2)

After the compound 3-1 (1.18 mmol) was dissolved in THF (10 ml), the solution was adjusted to a pH 4 with 1N aqueous hydrochloric acid. The mixture was stirred at room temperature for 30 minutes. To the mixture was added ethyl acetate (10 mL) and water (10 mL). The formed aqueous layer was neutralized to a pH 9 with 1N aqueous sodium hydroxide solution, and then extracted several times with ethyl acetate. After the organic layer thus obtained was dried over anhydrous magnesium sulfate and filtered, the filtrate was concentrated under reduced pressure. The concentrate was purified by column chromatography (eluent: hexane/ethyl acetate=2/1) to yield the title compound 3-2.

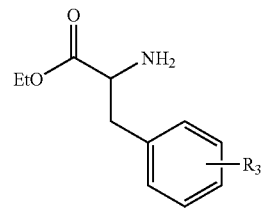

3-2

| Example-step | Compound No. | $R_3$ | Spectral data |
|---|---|---|---|
| 18-2 | 3-2a | 3,4-di-Me | $^1$H NMR(300 MHz, CDCl$_3$): δ 6.9–7.1 (m, 3H), 4.19 (q, 2H), 3.73 (m, 1H), 3.55 (dd, 1H), 3.17 (dd, 1H), 2.22 (m, 6H), 1.24 (m, 3H) |
| 19-2 | 3-2b | 4-t-Bu | $^1$H NMR(300 MHz, CDCl$_3$): δ 7.33 (d, 2H), 7.24 (d, 2H), 4.18 (q, 2H), 3.70 (m, 1H), 3.05 (dd, 1H), 2.83 (dd, 1H), 1.25 (m, 12H) |

Step 3: General Method for Synthesizing Compound (3-3)

After the compound 3-2 (0.68 mmol) was dissolved in dichloromethane (3 mL), the solution was cooled to 0° C. and (Boc)$_2$O (0.75 mmol) was added thereto. The reaction mixture was stirred at room temperature for 24 hours. The mixture was concentrated under reduced pressure. The resulting residue was purified by column chromatography (eluent: hexane/ethyl acetate=4/1) to yield the title compound 3-3.

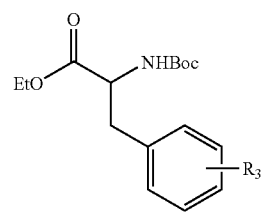

3-3

| Example-step | Compound No. | $R_3$ | Spectral data |
|---|---|---|---|
| 18-3 | 3-3a | 3,4-di-Me | $^1$H NMR(300 MHz, CDCl$_3$): δ 6.9–7.2 (m, 3H), 4.97 (m, 1H), 4.50 (m, 1H), 4.15 (q, 2H), 3.05 (m, 2H), 2.22 (m, 6H), 1.42 (s, 9H), 1.20 (t, 3H) |
| 19-3 | 3-3b | 4-t-Bu | $^1$H NMR(300 MHz, CDCl$_3$): δ 7.31 (d, 2H), 7.06 (d, 2H), 4.56 (m, 1H), 4.18 (q, 2H), 3.05 (d, 2H), 1.41 (s, 9H), 1.29 (s, 9H), 1.19 (t, 3H) |

Step 4: General Method for Synthesizing Compound (3-4)

After lithium aluminum hydride (1.79 mmol) was suspended in diethyl ether (5 mL), the suspension was cooled to 0° C. and a solution of the compound 3-3 (0.48 mmol) in diethyl ether (5 mL) was added thereto by dropping. After the reaction mixture was stirred at room temperature for 5 hours, the mixture was cooled to 0° C. again. Water (700 μl), NaOH (1.4 mL) and water (2.1 mL) were added to the mixture in succession, and stirred continuously. After the resulting mixture was washed with ethyl acetate and filtered, the obtained filtrate was concentrated under reduced pressure. The resulting residue was purified by column chromatography (eluent: ethyl acetate/hexane=4/1) to yield the title compound 3-4.

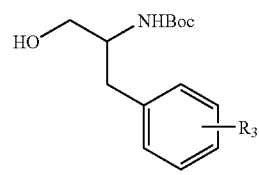

3-4

| Example-step | Compound No. | $R_3$ | Spectral data |
|---|---|---|---|
| 18-4 | 3-4a | 3,4-di-Me | $^1$H NMR(300 MHz, CDCl$_3$): δ 6.9–7.2 (m, 3H), 4.71 (bs, 1H), 3.83 (m, 1H), 3.5–3.7 (m, 2H), 2.85 (dd, 2H), 2.24 (m, 6H), 1.41 (s, 9H) |
| 19-4 | 3-4b | 4-t-Bu | $^1$H NMR(300 MHz, CDCl$_3$): δ 7.32 (d, 2H), 7.13 (d, 2H), 4.71 (bs, 1H), 3.87 (m, 1H), 3.5–3.7 (m, 2H), 2.79 (d, 2H), 1.41 (s, 9H), 1.30 (s, 9H) |

Step 5: General Method for Synthesizing Compound (3-5)

A mixture of the compound 3-4 (0.71 mmol), triethylamine (2.8 mmol) and a catalytic amount of 4-dimethylaminopyridine (DMAP) was dissolved in dichloromethane (7 mL), cooled to 0° C., and then trimethylacetyl chloride (2.8 mmol) was added thereto. The reaction mixture was stirred at room temperature for 1 hour. The mixture was diluted with dichloromethane, washed with 1N HCl, water and saturated aqueous sodium chloride solution once in succession, dried over anhydrous magnesium sulfate and filtered. The obtained filtrate was then concentrated under reduced pressure. The resulting residue was purified by column chromatography (eluent: ethyl acetate/hexane=1/4) to yield the title compound 3-5.

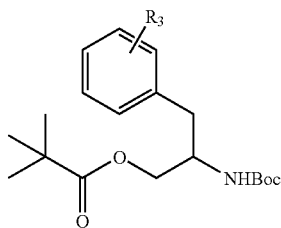

3-5

| Example-step | Compound No. | $R_3$ | Spectral data |
|---|---|---|---|
| 18-5 | 3-5a | 3,4-di-Me | $^1$H NMR(300 MHz, CDCl$_3$): δ 6.9–7.2 (m, 3H), 4.61 (bs, 1H), 4.01 (m, 3H), 2.86 (m, 2H), 2.24 (m, 6H), 1.41 (m, 9H), 1.23 (m, 9H) |
| 19-5 | 3-5b | 4-t-Bu | $^1$H NMR(300 MHz, CDCl$_3$): δ 7.30 (d, 2H), 7.10 (d, 2H), 4.57 (bs, 1H), 4.13 (m, 3H), 2.78 (m, 2H), 1.41 (m, 9H), 1.2–1.3 (m, 18H) |

Step 6: General Method for Synthesizing Compound (3-6)

The compound 3-5 (0.71 mmol) was dissolved in dichloromethane (6 mL), cooled to 0° C., and then trifluoroacetic acid (1.5 mL) was slowly added thereto. The reaction mixture was stirred at room temperature for 3 hours. The mixture was concentrated under reduced pressure to yield the unpurified title amine salt 3-6.

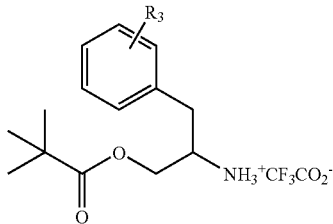

3–6

| Example-step | Compound No. | $R_3$ | Spectral data |
|---|---|---|---|
| 18-6 | 3–6a | 3,4-di-Me | $^1$H NMR(300 MHz, CDCl$_3$): δ 7.37(d, 1H), 7.13 (m, 2H), 4.1–4.3(m, 2H), 3.71(m, 1H), 3.04(m, 2H), 2.22(m, 6H), 1.22(m, 9H) |
| 19-6 | 3–6b | 4-t-Bu | $^1$H NMR(300 MHz, CDCl$_3$): δ 7.35(m, 2H), 7.13 (m, 2H), 4.1–4.2(m, 3H), 2.80(d, 2H), 1.30(s, 9H), 1.09(s, 9H) |

Step 7: Method for Synthesizing Compounds (3-7 and 3-8)

To a solution of compound 3-6 (0.46 mmol) in dimethylformamide (1 mL) was added triethylamine (0.46 mmol). The resulting mixture was stirred at room temperature under nitrogen for 30 minutes. To the mixture was added the compound 2-8 (0.46 mmol), and stirred at room temperature for 24 hours. The reaction mixture was diluted with water, and extracted several times with ethyl acetate. The obtained organic layer was washed with water and brine, dried over anhydrous magnesium sulfate, and then concentrated under reduced pressure. The resulting residue was purified by column chromatography (eluent: hexane/ethyl acetate=1/1) to yield the title compounds 3-7 or 3-8.

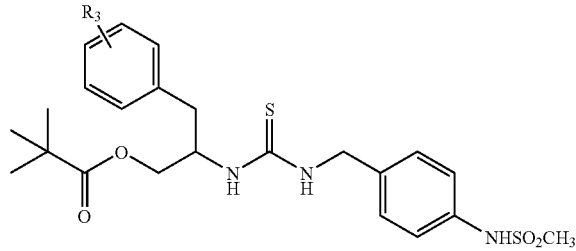

3–7 or 3–8

| Example-step | Compound No. | $R_3$ | Spectral data |
|---|---|---|---|
| 18-7 | 3–7 | 3,4-di-Me | $^1$H NMR(300 MHz, CDCl$_3$): δ 7.19(m, 4H), 7.04 (m, 3H), 6.28(brs, 1H), 6.07(brs, 1H), 4.56(m, 2H), 4.17(m, 1H), 3.99(m, 1H), 3.01(m, 5H), 2.76 (m, 1H), 2.26(m, 6H), 1.19(s, 9H) |
| 19-7 | 3–8 | 4-t-Bu | $^1$H NMR(300 MHz, CDCl$_3$): δ 7.27(m, 8H), 6.68 (brs, 1H)6.51(brs, 1H), 6.11(m, 1H), 4.58(m, 2H), 4.20(m, 1H), 3.99(m, 1H), 3.12(m, 5H), 2.76(m, 1H), 1.30(m, 18H) |

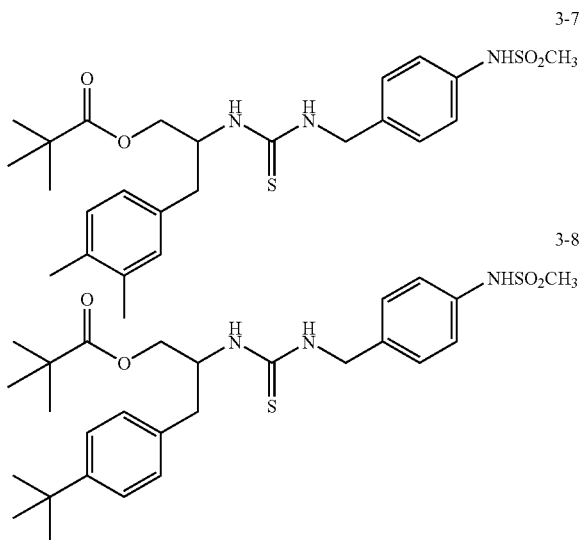

EXAMPLES 20~23

General Method for Synthesizing Compounds (4-1~4-4)

A solution of amine compound (0.5 mmol) and (4-methanesulfonylaminophenyl)acetic acid pentafluorophenyl ester (0.5 mmol) in dichloromethane was stirred at room temperature for 24 hours. The reaction mixture was concentrated under reduced pressure. The resulting residue was purified by column chromatography (eluent: hexane/ethyl acetate=1/2) to yield the title compounds 4-1~4-4.

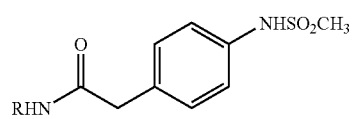

4-1~4-4

| Examples | Compound No. | R | Spectral data |
|---|---|---|---|
| 20 | 4-1 | 4-t-BuPhCH$_2$— | $^1$H NMR(300 MHz, CDCl$_3$): δ 7.1–7.3(m, 8H), 6.44(brs, 1H), 5.66(brs, 1H), 4.40 (d, 2H), 3.57(s, 2H), 3.00(s, 3H), 1.30 (s, 9H); mp = 54° C. |
| 21 | 4-2 | 3,4-di-Ph(CH$_2$)$_2$— | $^1$H NMR(300 MHz, CDCl$_3$): δ 7.1–7.3 (m, 4H), 6.43(brs, 1H), 5.35(m, 3H), 3.52(s, 2H), 3.21(q, 2H), 3.02(s, 3H), 2.00(d, 4H) 1.56(s, 2H), 1.26(s, 22H), 0.88(t, 3H); mp = 134° C. |
| 22 | 4-3 | Oleyl | $^1$H NMR(300 MHz, CDCl$_3$): δ 7.23(m, 4H), 7.04(d, 1H), 6.87(m, 2H), 6.38(brs, 1H), 5.32(brs, 1H), 3.49(s, 2H), 3.25(q, 2H), 3.01(s, 3H), 2.52(t, 2H), 2.22(s, 6H), 1.77(t, 2H) |
| 23 | 4-4 | ![structure] | $^1$H NMR(300 MHz, CDCl$_3$): δ 7.1–7.3(m, 4H), 6.8–7.1(m, 3H), 5.90(t, 1H), 4.13 (m, 1H), 3.80(m, 1H), 3.54(s, 2H), 3.35 (m, 1H), 3.11(m, 1H), 2.97(s, 3H), 2.5–2.7(m, 2H), 2.1–2.3(m, 7H), 1.24(s, 9H); mp = 30° C. |

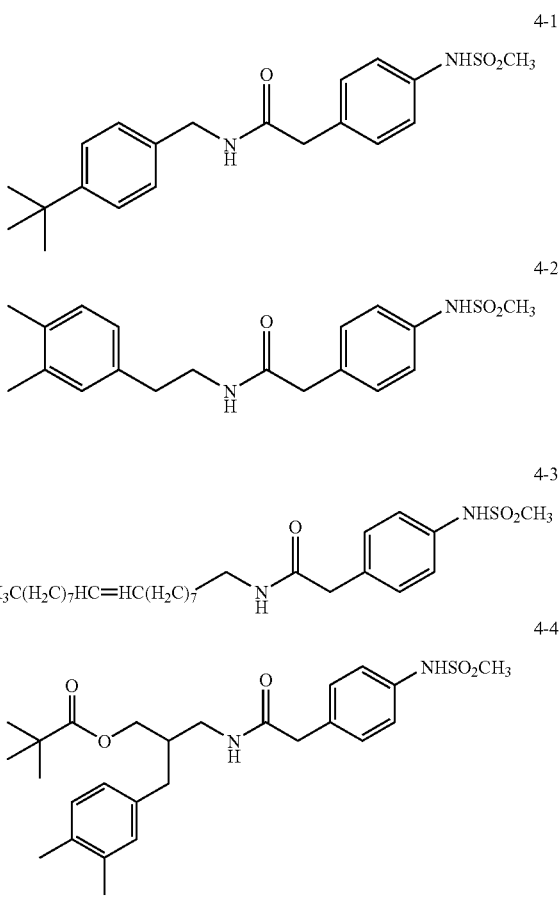

In the below, it is confirmed by calcium influx test that the compounds of the present invention are antagonist to vanilloid receptor, further confirmed by analgesic effect test that they exhibit strong analgesic effects while showing no initation shown in an agonist.

Experimental Example, Biological Potency Test (1) $^{45}$Ca Influx Test

1) Separation of Spinal Dorsal Root Ganglia (DRG) in Newborn Rats and Primary Culture Thereof Neonatal(2-day old or younger than 2-day old) SD rats were put in ice for 5 minutes to anesthetize and disinfected with 70% ethanol. DRG of all part of spinal cord were dissected (Wood et al., 1988, J. Neurosci. 8, pp3208–3220) and collected in DME/F12 medium to which 1.2 g/l sodium bicarbonate, 50 mg/l gentamycin were added. The DRG were incubated sequentially at 37° C. for 30 min in 200 U/ml collagenase and 2.5 mg/mil trypsin, separately. The ganglia were washed twice with DME/F12 medium supplemented with 10% horse serum, triturated through a fire-polished Pasteur pipette, filtered through Nitex 40 membrane to obtain single cell suspension. This was subjected to centrifugation, then re-suspended in cell culture medium at certain level of cell density. As the cell culture medium, DME/F12 medium supplemented with 10% horse serum, diluted 1:1 with identical medium conditioned by C6 glioma cells (2 days on a confluent monolayer) was used, and NGF(Nerve Growth Factor) was added to final concentration of 200 ng/ml. After the cells were grown 2 days in medium where cytosine arabinoside (Ara-C, 100 μM) was added to kill dividing nonneuronal cells, medium was changed to one without Ara-C. The resuspended cells were plated at a density of 1500–1700 neurons/well onto Terasaki plates previously coated with 10 μg/ml poly-D-ornithine.

2) $^{45}$Ca Influx Experiments

DRG nerve cells from the primary culture of 2–3 days were equilibrated by washing 4 times with HEPES (10 mM, pH 7.4)-buffered $Ca^{2+}$, $Mg^{2+}$-free HBSS (H-ABSS). The solution in each well was removed from the individual well. Medium containing the test compound plus capsaicin (final concentration 0.5 μM) and $^{45}$Ca (final concentration 10 μCi/ml) in H-HBSS was added to each well and incubated at room temperature for 10 min. Terasalki plates were washed six times with H-HBSS and dried in an oven. To each well, 0.3% SDS (10 μl) was added to elute $^{45}$Ca. After the addition of 2 ml of scintillation cocktail into each well, the amount of $^{45}$Ca influx into neuron was measured by counting radioactivity. Antagonistic activities of test compounds against vanilloid receptor were calculated as percent of the maximal response of capsaicin at a concentration of 0.5 μM and results are given as $IC_{50}$ (Table 1).

(2) Channel Activity Assay

Antagonistic activities of test compounds were assayed based on electrical change of cation channel connected to vanilloid receptor and experiments were conducted according to reference method (Oh et al, 1996, J. Neuroscience 16, pp1659–1667) (Table 1).

TABLE 1

Results of Calcium Influx and Patchclamp Test

| Examples | Calcium Uptake Test($IC_{50}$) | Patchclamp Test (antagonistic activities) |
|---|---|---|
| 1 | 0.45 | ++ |
| 2 | 2.5 | |
| 3 | 4.3 | |
| 4 | 32 | |
| 5 | >50 | |
| 6 | 11 | |
| 7 | NR | |
| 8 | NR | |
| 9 | 13 | |
| 10 | 2.5 | |
| 11 | >50 | |
| 12 | 0.68 | |
| 13 | 38 | |
| 14 | 2.8 | |
| 15 | >50 | |
| 16 | 1.1 | |
| 17 | 1.8 | |

NR: no response
+: antagonistic potency equal to capsazepine
++: antagonistic potency 10 times higher than capsazepine (3) Analgesic Activity Test: Mouse Writhing Test by Inducing with Phenyl-p-quinone Male ICR mice (mean body weight 25 g) were maintained in a controlled lighting environment (12 h on/12 h off for experiment. Animals received an intraperitoneal injection of 0.3 ml of the chemical irritant phenyl-p-quinone (dissolved in saline containing 5% ethanol to be a dose of 4.5 mg/lkg) and 6 min later, the number of abdominal constrictions was counted in the subsequent 6 min period. Animals (10 animals/group) received 0.2 ml of test compounds solution in vehicle of ethanol/Tween 80/saline (10/10/80) intraperitoneally 30 min before the injection of phenyl-p-quinone. A reduction in the number of writhes responding to the test drug compound relative to the number responding in saline control group was considered to be indicative of an analgesic effect. Analgesic effect was calculated by % inhibition equation (% inhibitio=(C−T)/C×100), wherein C and T represent the number of writhes in control and compound-treated group, respectively (Table 2).

The test results demonstrated that analgesic effect of the compounds used in this experiment is potent, and in particular, it is significant to clarify that vanilloid receptor antagonist can exhibit such potent analgesic effect, and the results suggests that vanilloid receptor antagonist has potential as an analgesic agent.

TABLE 2

Test result of analgesic activity for writhing by phenyl-p-quinone

| Examples | Dose (mg/kg) | Analgesic effect (% Inhibition) |
|---|---|---|
| 1 | 1 | 50 |
| 12 | 1 | 65 |

(4) Antiinflammatory Activity Test: TPA(12-O-tetradecanoylphorbol 13-acetate)-induced Mouse Ear Edema Test Male ICR mice(body weight 25–30 g), 10 animals/group, were treated topically on the right ear with 30 μl of TPA (2.5 μg) solution in acetone and after 15 min. 30 μl of acetone or test compound solution in acetone was applied topically. After six hours, an identical treatment was applied again. After twenty four hours following the treatment of TPA, the animals were sacrificed and ear tissue was dissected using 6 mm-diameter punch. Ear tissue dissected were weighed to the nearest 0.1 mg on an electrobalance. The increased weight of the tissue compared to control group was considered as an index of inflammation. The percent inhibition is defined by the following equation:

% inlibition=(C−T)/C×100, wherein C and T represent an increase of ear weight in TPA-treated and TPA+drug-treated group, respectively.

The above experiment shows that vanilloid receptor antagonist exhibits significant anti-inflammatory effects. This phenomenon can be understood by connecting with the action of vanilloid receptor in neurogenic inflammation, and suggests potential applicability of vanilloid receptor antagonist in various inflammatory diseases, in particular, neurogenic inflammatory diseases.

TABLE 3

TPA-induced mice ear edema test

| Examples | Dose (mg/ear) | Anti-inflammatory effect (% Inhibition) |
|---|---|---|
| 1 | 1 | 34 |
| 12 | 1 | 41 |

INDUSTRIAL APPLICABILITY

The compounds according to the present invention are useful in the prevention or treatment of pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder such as asthma and chronic obstructive pulmonary diseases, irritation in skin, eye or mucous membrane, stomach-duodenal ulcer, inflammatory bowel disease, inflammatory disease, etc.

The invention claimed is:

1. A compound of formula I:

$$\text{(I)}$$

or a pharmaceutically acceptable salt thereof,
wherein,
X represents a sulfur atom or an oxygen atom;
$R_1$ represents a lower alkyl sulfonyl group having 1 to 5 carbon atoms, an aryl sulfonyl group or a lower alkyl carbonyl group having 1 to 5 carbon atoms, which may be unsubstituted or substituted with a halogen atom;
$R_2$ represents a hydrogen atom, a methoxy group or a halogen atom;

when A is —NHCH$_2$—, B represents wherein, n is 0 or 1, or when A is —CH$_2$—, B represents 4-t-butylbenzyl, 3,4-dimethylphenylethyl, or an oleyl group;
Y represents —CH$_2$— or —CH$_2$CH$_2$—;
$R_3$ represents a hydrogen atom or a lower alkyl group having 1 to 5 carbon atoms; and
$R_4$ represents a lower alkyl group having 1 to 5 carbon atoms or a phenyl group.

2. A pharmaceutical composition comprising the compound of formula I according to claim 1 or a pharmaceutically acceptable salt thereof as an active ingredient together with a pharmaceutically acceptable carrier.

3. A method for treating a condition related to vanilloid receptor, wherein the method comprises administering to a person in need thereof a therapeutically effective amount of a compound of formula I of claim 1 or a pharmaceutically acceptable salt thereof and wherein the condition related to vanilloid receptor is pain, acute pain, chronic pain, neuropathic pain, post-operative pain, migraine, arthralgia, neuropathies, nerve injury, diabetic neuropathy, neurodegeneration, neurotic skin disorder, stroke, urinary bladder hypersensitiveness, irritable bowel syndrome, a respiratory disorder, asthma, chronic obstructive pulmonary disease, irritation of skin, eye or mucous membrane, fervescence, stomach-duodenal ulcer, inflammatory bowel disease or inflammatory diseases.

4. A compound or a pharmaceutically acceptable salt thereof according to claim 1, wherein, X represents a sulfur atom;

$R_1$ represents a lower alkyl sulfonyl group having 1 to 5 carbon atoms;

$R_2$ represents a hydrogen atom or a methoxy group;

A is —NHCH$_2$—;

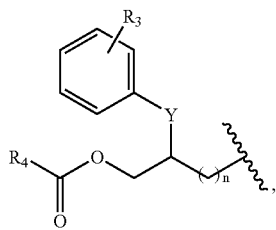

B represents $R_4$ wherein n is 0 or 1 and Y represents —CH$_2$— or —CH$_2$CH$_2$—;

$R_3$ represents a hydrogen atom or a lower alkyl group having 1 to 5 carbon atoms; and $R_4$ represents a lower alky group having 1 to 5 carbon atoms.

5. A compound or a pharmaceutically acceptable salt thereof according to claim 1, wherein the compound is:

N-[2-(3,4-Dimethylbenzyl)-3-(pivaloyloxy)propyl]-N'-[4-(methanesulfonylamino) benzyl]thiourea;

N-[2-(3,4-Dimethylbenzyl)-3-(pivaloyloxy)propyl]-N'-[3-methoxy-4-(methanesulfonylamino)benzyl]thiourea;

N-[4-(4-tert-Butylphenyl)-2-(pivaloyloxymethyl)-butyl]-N'-[4-(methanesulfonyl-amino)benzyl]thiourea;

N-[3-(3,4-Dimethylphenyl)-1-pivaloyloxy-2-propyl]-N'-[4-(methanesulfonyl-amino)benzyl]thiourea;

N[3-(4-tert-Butylphenyl)-1-pivaloyloxy-2-propyl]-N-[4-(methanesulfonyl-amino)benzyl]thiourea;

N-(4-tert-Butylbenzyl)-2-[4-(methanesulfonylamino) phenyl]acetamide; or

N-[2-(3,4-Dimethylbenzyl)-3-(pivaloyloxy)propyl]-2-[4-(methanesulfonyl-amino)phenyl]acetamide.

6. A compound or a pharmaceutically acceptable salt thereof according to claim 5, wherein the compound is:

N-[2-(3,4-Dimethylbenzyl)-3-(pivaloyloxy)propyl]-N'-[4-(methanesulfonylamino)benzyl]thiourea; or N-[2-(3,4-Dimethylbenzyl)-3-(pivaloyloxy)propyl]-N'-[3-methoxy-4-(methanesulfonylamino)benzyl]thiourea.

* * * * *